United States Patent [19]
Gazitt

[11] Patent Number: 5,480,825
[45] Date of Patent: Jan. 2, 1996

[54] AG-F HUMAN T CELL LINE WITH UNIQUE PHENOTYPE AND CYTOKINE SECRETIONS

[76] Inventor: Yair Gazitt, 14507 Beack Bear Dr., Little Rock, Ark. 72212

[21] Appl. No.: 116,885

[22] Filed: Sep. 2, 1993

[51] Int. Cl.$^6$ ........................................ C12N 5/08
[52] U.S. Cl. .................. 435/240.25; 435/240.1; 435/240.2
[58] Field of Search ............... 435/2, 7.21, 7.24, 435/240.1, 240.2, 240.25

[56] References Cited

PUBLICATIONS

Protti et al., Use of synthetic peptides . . . J. of Immunology, 1990; vol. 144; 1711–1720.
Kawasaki et al., Both granulocyte–macrophage . . . Exper. Hematology, 1990; vol. 18; 1090–1093.
Sivanandham & Mukerji, Functionally Different HTLV . . . Immunology Letters, 1989/1990; vol. 23; 149–154.
Casareale & Volsky, A T lymphoblastoid cell line . . . Cell Biology Int'l Reports, Dec. 1985; vol. 9, No. 2; 1057.
Lanfrancone et al., Release of heopoietic factors . . . J. of Cellular Phys., 1985; vol. 122; 7–13.
Britten & Hudson, Isolation and characterization of human T cell line . . . , The Lancet, Sep. 1985; 637–639.
Goldberg et al., Cloned allospecific human helper . . . J. of Immunology, 1985; vol. 135, No 2: 1012–1019.
Nutman et al., Filarial parasite–specific T cell . . . J. of Immunology, 1985; vol. 134 No. 2; 1178–1184.
Tsui et al., Characterization of a long–term . . . Cellular Immunology, 1984; vol. 85; 34–44.
Clark et al., Generation of phenotypic helper/inducer . . . Cellular Immunology, 1984; vol. 84; 409–414.
Mozes, An insight into the T–cell . . . Ann. Immunology, 1983; vol. 134; 123–131.
Hoshino et al., Establishment and characterization . . . Proc. Natl. Acad. Sci. USA, 1983; vol. 80; 6061–6065.
Fischer et al., Induction of a T–cell–mediated . . . Immunology, 1983; vol. 48; 177–186.
Zanders et al., Antigen–specific and non–specific . . . Immunology, 1983; vol. 48; 361–366.
Friedman & Thompson, Functionally restricted, allospecific . . . J. of Exp. Med., 1983; vol. 157; 1675–1680.
Lanzayecchia et al., Human T cell lines with antigen . . . Eur. J. Immunology, 1982; vol. 12; 468–474.
Fischer et al., An influenza virus matrix protein–specific . . . Eur. J. Immunology, 1982; vol. 12; 844–849.
Friedman et al., OT–CLL: A human T cell . . . The Journal of Immunology, 1982; vol. 128, No. 2;035–940.
Fischer et al., Long–term human T–helper lines . . . Nature, Nov. 1981; vol. 294: 166–168.
Haynes et al., Phenotypic characterization of cutaneous . . . The New England J. of Med., vol. 304, No. 22; 1319–132.
Gazitt et al., Isolation and Characterization of an Early T–Helper/Inducer Cell Line with a Unique Pattern of Surface Phenotype, Constitutive Cytokine Secretion and Myc Oncogene Expression, Leukemia, vol. 7, No. 12 (Dec.) 1993, pp. 2034–2044.
I. Gazitt et al. Proc. Annu Meet Am Assoc Cancer Res A256 (1993).

Primary Examiner—David L. Lacey
Assistant Examiner—Phillip Gambel
Attorney, Agent, or Firm—Joan R. Owen

[57] ABSTRACT

A human T cell line, designated AG-F, the cells of which: a) are capable of adherent growth as well as growth in suspension; b) have a short doubling time of approximately eight to nine hours; c) are near tetraploid, containing eighty-five to eighty-seven chromosomes instead of the usual forty-six; d) exhibit properties similar to those exhibited by T cells in very early stages of development; e) secrete a great variety of interleukins; and f) exhibit high CD4 antigen production, and the utilization of the AG-F cell line in hybridoma technology, including but not limited to lymphokine secretion studies, T cell lymphotropic virus studies, augmentation of antibody secretion in hybridomas and augmentation of cell growth and mitotic index by AG-F conditioned medium studies.

1 Claim, 10 Drawing Sheets

Fig. 9A
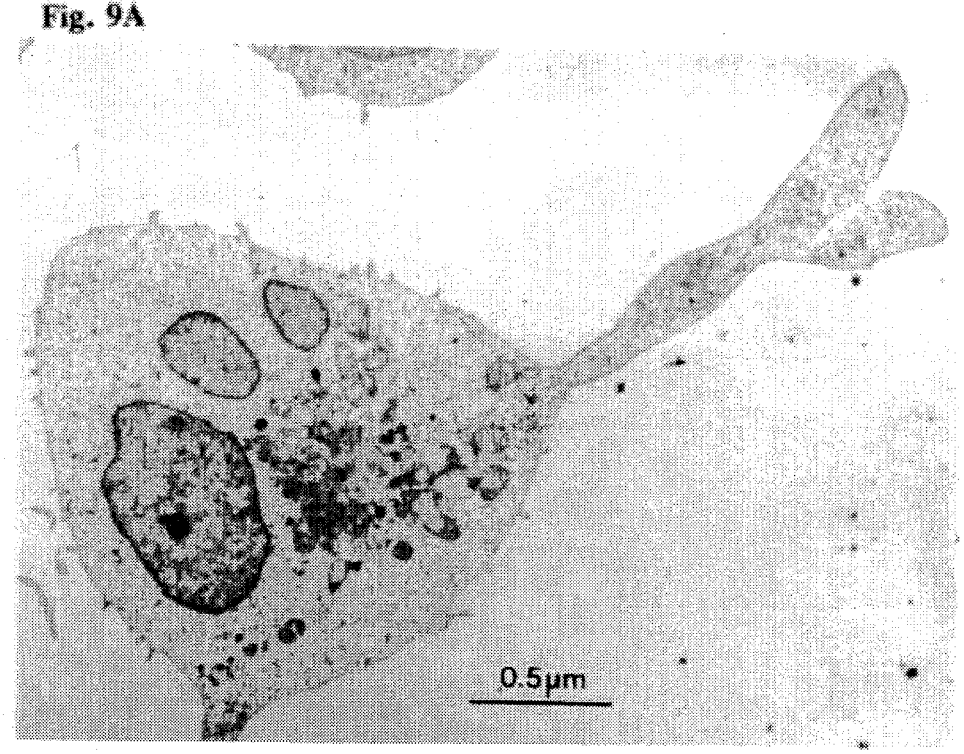
Fig. 9B
Fig. 9C
Fig. 9D

AG-F HUMAN T CELL LINE WITH UNIQUE PHENOTYPE AND CYTOKINE SECRETIONS

The present invention relates generally to a human T cell line and more specifically to a human T cell line with a unique pattern of surface markers and lymphokine secretions as well as the ability to grow in serum-free culture medium.

BACKGROUND OF THE INVENTION

T cells are critical in the regulation of all cell-mediated immune reactions. The antigen-specific interactions mediated by T cells and antigen-presenting cells determine the antigen specificity of the cellular immune responses. However, T cells also interact with other cells via lymphokines which they release following activation. Although the actions of lymphokines are antigen non-specific, they usually act with greatest effect on cells in the immediate vicinity of the active T cells. Thus lymphokines can act as mediators of antigen-specific immune reactions. Isolation and identification of lymphokines secreted by T cells are very important steps in the advancement of biomedical research.

Many of the advances in biomedical research come from the use of continuous culture of cells from different tissue origin. There is a need for a continuous human T cell line to permit the search for production of novel cytokines and to permit the screening of compounds to determine their effects on T cells.

SUMMARY OF THE INVENTION

The present invention provides a human T cell line, which is designated AG-F, the cells of which: a) are capable of adherent growth as well as growth in suspension, b) capable of growth in serum-free medium, c) have a short doubling time of approximately eight to nine hours, d) are near tetraploid, containing eighty-five to eighty-seven chromosomes instead of the usual forty-six, e) exhibit properties similar to those exhibited by T cells in very early stages of development, f) secrete a great variety of interleukins, g) exhibit high CD4 production, and h) over express a great variety of oncogenes: c-myc, N-myc, P53, and N-RAS. The present invention also provides a process for producing lymphokines, comprising culturing cells of a human T cell line, which cells are capable of reproducibly and indefinitely propagating in serum-supplemented or in serum-free culture medium and which produce lymphokines, harvesting fluid from the culture, and isolating lymphokines from the harvested fluid.

It is an object of the present invention to provide a continuous T cell line, which can grow and replicate in vitro. AG-F cell line can be subcultured continuously and indefinitely.

Another object of the present invention is to provide a novel cell line useful in the study of immune reactions. AG-F cell line is important to permit the study of biochemical, physiological, and pharmacological factors that regulate the function of immune reactions and to permit the study of growth and differentiation and apoposis by oncogenes.

Yet another object of the present invention is to provide a process for producing lymphokines. AG-F cells produce a great variety of lymphokines.

BRIEF DESCRIPTION OF THE DRAWINGS

The above and other objects, features and advantages of the present invention will become apparent from the following description of the invention and the appended claims, taken in conjunction with the accompanying drawings, in which:

FIGS. (1A–F) are micrographs of the cells of the present invention variously stained and magnified 400 times;

FIGS. 9(A–D) depict the ultrastructure of adherent cells of the present invention; and FIG. 10 is a Northern Blot analysis depicting the expression of mRNA transcripts to oncogenes.

DETAILED DESCRIPTION OF THE PRESENTLY PREFERRED EXEMPLARY EMBODIMENT

Figure 1A:
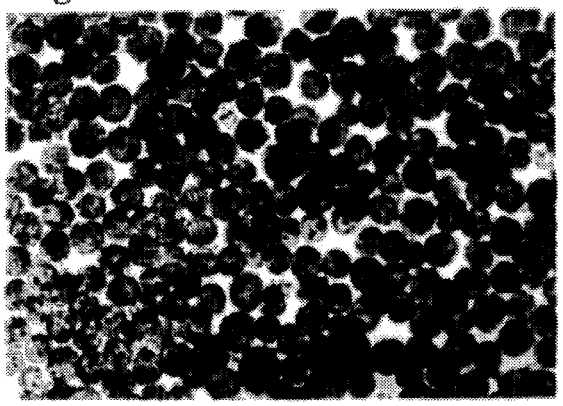
Figure 1B:
Figure 1C:
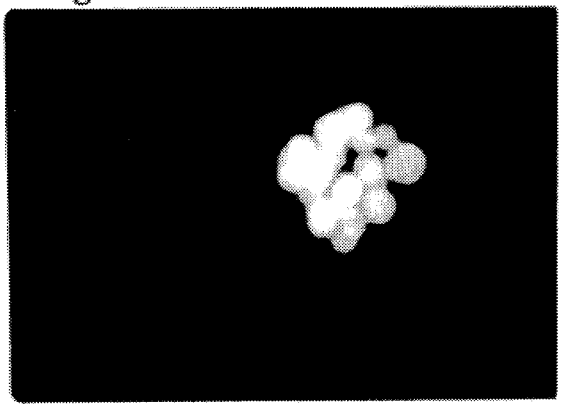
Figure 1D:
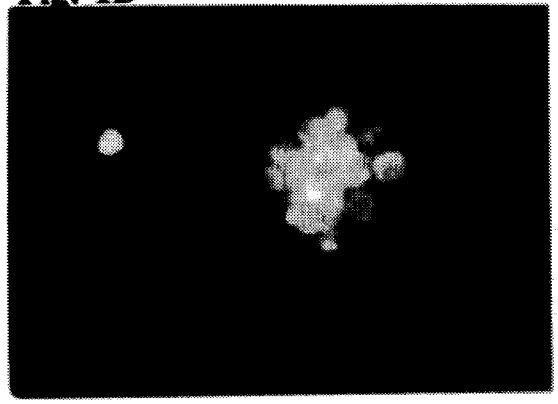
Figure 1E:
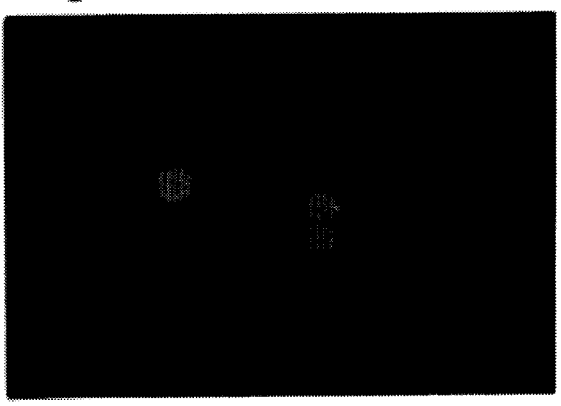
Figure 1F:
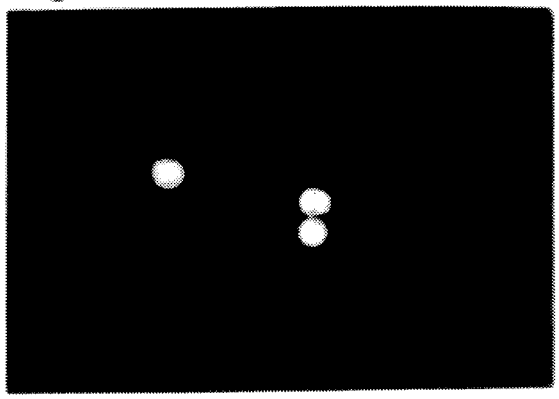

The AG-F T cell line of the present invention, deposited on Jun. 29, 1993, under the provisions of the Budapest Treaty at the American Type Culture Collection, Rockville, Md. as cell line CRL 11391, will be more specifically described below in connection with the following materials and methods:

1. Antibodies:

Anti c-myc antibody (IgG1) was obtained from hybridoma tissue culture of an NCI clone specific for amino acid peptide residue 171–188 of the c-myc oncoprotein.

Anti N-myc antibody (IgM) was generated in my laboratory by immunization of BALB/C mice with N-myc specific amino acid peptide residue 336–348 [Gazitt Y, He Y-J, Erdos G, Chang L, Ashtorab H, Cohen R J. Development of two color stain and immunolocalization method for N-myc and c-myc oncoprotein with a newly generated mouse IgM anti N-myc antibody. *J Immunol Methods* 1992; 148: 159–169.].

Anti-NB antibodies-UJ13A and H11 (anti-N-CAM; antibody 127.1 (anti-L-1), anti-THY-1 and M340, all specific for neuronal cells, were obtained from Dr. John Kemshead, Bristol, UK. Staining was done as described before [Gazitt Y, He Y-J, Graham-Pole J. A novel methodology for the establishment of neuroblastoma cell lines from metastatic marrow. Expressions of surface markers, neurofilaments, MDR-1 and myc proteins. *J Immunol Methods* 1992; 148: 171–178.].

Antibodies for immunophenotyping: Antibodies to CD4(FITC); CD8(PE); CD34(PE); CD45(PERCP); CD20(PERCP); CD3(PERCP); CD56(PE); CD11b(PE); CD11c(PE); and CD38(PE) were purchased from Becton Dickinson (Mountain View, Calif.). Antibodies to CD2(PE);

CD45RA(FITC); CD14(FITC); CD15(FITC); CD25(FITC); CD7(FITC); CD5(PE); CD71(FITC and TdT(FITC) were purchased from Gentrak, Inc. (Plymouth Meeting, Pa.). Antibodies to CD1a(PE); CD29(PE); CD13(PE) and CD33(PE) were purchased from Coulter Cytometry (Hialeah, Fla.). Antibodies to CD10(FITC/PE); CD45RO-FITC and CD30(FITC) were purchased from Dako Corporation (Carpinteria, Calif.).

2. Immunofluorescence Staining:

a) Staining for N-myc and c-myc oncoproteins:

Staining was carried out as previously described [*J Immunol Methods* 1992; 148:159–169, *J Immunol Methods* 1992; 148:171–178, and Gazitt Y, He Y-J, Chang L, Koza S, Fisk D, Graham-Pole J. Expression of N-myc, c-myc and MDR-1 proteins in newly established neuroblastoma cell lines: A study by immunofluorescence staining and flow cytometry. *Cancer Res* 1992; 52: 2957–2965.]. Mouse IgG and mouse IgM controls at five fold immunoglobulin excess, were used for each staining combination to determine non-specific binding. All cell staining was performed at antibody-saturating concentrations. Fluorescent cells were viewed and micrographs were taken using a Nikon fluorescence microscope equipped with an FX-35 camera and automatic exposure device AFX-II. A green filter was used for FITC and a red filter was used for phycoerythrin stained cells.

b) Staining for Surface Markers

Staining was performed on viable, intact cells removed from culture and washed 2x in PBS. Saturating concentrations of antibodies conjugated with fluorescein isothiocyanate (FITC), phycoerythrin (PE), or peridinin chlorophyll (PERCP) were added to $1-2 \times 10^6$ cells and incubated for 20 min. at 4° C. Unbound antibody was removed by washing the cells 2x in PBS+2% FCS. Appropriate isotypic controls for all three fluorochromes were used with each three color combination. Fluorescence intensity for all three fluorochromes was standardized daily using Full Spectrum beads (Flow Cytometry Standard Corporation, Research Triangle Park, N.C.) with compensation established using stained human lymphocytes. Ten thousand cell list mode files were collected using either FASCAN of FACSTAR (Becton Dickinson, Mountain View, Calif.) with analysis of data using the Lysys II program (Becton Dickinson).

3. Staining for nuclear DNA content:

for determining the distribution of cells within the cell cycle, cells were stained with PI and analyzed cytometrically using the Epics 752 (Coulter Cytometry, Hialeah, Fla.). The percent cells in $G_1$, S, and $G_2/M$ was derived from computer modeling of the single parameter histograms using the program Modfitt (Vertity Software House, Topsham, Me.).

4. Analysis of Cell Karyotype:

Karyotyping of AG-F cells was done by the Cytogenetic Laboratory of the University of Florida. Staining was done by the G-banding method (GTG) according to Seabright [Seabright M. A rapid banding technique for human chromosomes. *Lancet* 1971; 2:971–972.]. Twenty karyotypes were analyzed.

5. Gene Rearrangement Studies:

Immunoglobulin and T cell receptor gene rearrangement analyses were performed using Southern blot hybridization procedures. DNA was extracted by the phenol/chloroform method digested with restriction enzymes, electrophoresed in an agarose gel and transferred to a nylon membrane by vacuum blotting (Oncor, Gaithersburg, Md.). The membrane was hybridized to the JH probe and to the CT beta probe (Oncor) to detect immunoglobulin and T cell gene rearrangement, respectively. Placental DNA and DNA from another patient were also probed for comparison.

6. Lymphokine Secretion:

IL1-α, IL-8 and GM-CSF were determined by radioimmunoassay (RIA) using the Advanced Magnetic Kit (Cambridge, Mass.). IL1-β, IL-2 and IL-6 were determined by an enzyme linked immunoassay kit (ELISA), using the Advanced Magnetic kit. IL-3 was determined by an ELISA kit, using the Quantikine IL-3 kit (R&D Systems, Minneapolis, Minn.). IFN-gamma was determined by an ELISA kit (GIBCO-BRL, Grand Island, N.Y.). IL-4, IL-5, IL-10 and TNF-α were determined by ELISA (DNAX, Palo Alto, Calif.).

7. Northern Blots Analysis of mRNA for myc and Lymphokine Transcripts:

RNA was extracted from AG-f cells by a modification to the guanidine thiocyanate method described by W-Q Xie and L. I. Rothblum [Xie W-Q, Rothblum, L I. Rapid small scale RNA isolation from tissue culture cells. *Biotechniques* 1991; 11:325–327.]. RNA was electrophoresed in denaturing agarose gels transferred to nylon membrane and probed according to Maniatis [Maniatis T, Fritsch E F, Sambrook S. Molecular cloning: A laboratory manual. pp.149–172. Cold Spring Harbor, N.Y.: Cold Spring Harbor Laboratory Press, 1982.]. Probes for IL-1α; IL-1β; IL-2; IL-3; IL-4; IL-6; G-CSF; GM-CSF and MGF were provided by Immunex (Seattle, Wash.). Probes for c-myc, N-RAS, N-myc, P53, and actin were from Oncor (Oncor, Gaithersburg, Md.). The inserts were released from the plasmids by appropriate restriction enzymes and were labeled with $^{33}P$ by the random primer method using the BRL labelling kit (BRL, Bethesda, Md.). RNA extracted from HL-60 (promyelocytiic) and CHP126 (neuroblastoma) cell lines were used for comparison with AG-F.

8. Transmission Electron Microscopy (TEM):

Cell pellets were fixed with 2% glutaraldehyde in PBS for 30 min. at 4° C., washed in PBS and fixed again with 1% $O_sO_4$ in PBS, washed again and dehydrated by placing in increased concentrations of ethanol (10% to 100%), Cell pellets were then embedded in EPON 812 and ultrathin sections prepared. Sections were stained for 10 min. with 2% uranyl acetate, followed by staining with lead acetate. Sections were viewed and micrographs were taken using Hitachi 7000 electron microscope. Specimens were examined at 75 Kv.

9. Scanning Electron Microscopy (SEM):

Cells were fixed and dehydrated as described above for TEM, after which the cell pellet was dried in hexamethyl disilazane, spotter coated with gold and examined under Hitachi S-4000 microscope at 10 Kv.

10. Induction of Cell Adherence:

Cells were induced to adhere to the plastic by precoating 35 mm plates with 10 micrograms of fibronectin (Human Plasma, Sigma, St. Louis, Mo.) in 0.5 ml of PBS for 2 h at room temperature. PBS was then removed and 1 ml of cell suspension was added ($2 \times 10^5$/ml) in DMEM culture medium containing 10% FCS. Partial adherence (50–60%) and formation of processes (10%) was observed after 12–24 h. Process formation was maximal after incubation with phorbol myristate acetate (PMA, Sigma, St. Louis, Mo.) at 2 g/ml for 2–3 days, when all the cells were adherent and over 80% of the cells had processes larger than twice the size of the original cells. Similar treatment of plates with collagen (type I, Sigma) was done with 20 μg/plate with and without the addition of PMA at 2 μg/ml.

11. Staining with Hoechst, Fluorescein Diacetate, Rhodamine 123 and Giemsa:

Staining with Hoechst 33252 (Sigma, St. Louis, Mo.) was done by brief (4 min.) exposure of plates to 1 µg/ml of the dye (final concentration in DMSO). Staining with Rhodamine 123 and fluorescein diacetate (FDA, Sigma) was done similarly to Hoechst staining with 10 µg/ml and 5 µg/ml of the rhodamine and FDA dyes, respectively. Staining with Giemsa stain (GIBCO) was done on cytospinned, methanol fixed cells. Adherent cells were fixed and stained directly on the plate. Cells were viewed and micrographs were taken as described above.

The T cell line of the present invention will hereinafter be described by the following Examples. However, it is to be understood that the present invention is not limited thereto.

EXAMPLE 1

Isolation and long term culture of AG-F cell line

AG-F cell line was isolated from the bone marrow of a patient who was diagnosed as Stage 4 neuroblastoma with metastases to the bone marrow. The patient was undergoing myeloablative treatment and autologous bone marrow rescue and developed secondary Hodgkins lymphoma. AG-F cancer cells were co-isolated with neuroblastoma cells in the process of the establishment of the neuroblastoma line. AG-F cells grow in clusters of fifty to two hundred cells in suspension. Optimal growth was achieved in Dulbeco Modified Essential Medium containing ten percent calf serum (DMEM; GIBCO, Grand Island, N.Y.). AG-F cells could grow easily in RPMI medium containing ten percent calf serum. Cells seeded at $2\times10^5$ cells/ml may reach up to five cell doublings in three days, with a population doubling of nine hours in the logarithmic phase, where clusters of 100–200 cells are very common. For best growth conditions cells were transferred every two to three days and seeded at $2-5\times10^5$ cells/ml. The cells can easily be adapted to grow in serum free medium (Ex Vivo, Whittaker, Bethesda, Md.), where the population doubling time increases to about twenty hours.

Cell morphology and ultrastructure

FIG. 1 (C,D) is an example of a cluster of about thirty cells stained with the vital stains fluorescein diacetate (C; green) and Hoechst (D; blue, for nuclear stain). Stained with the Giemsa stain (FIG. 1A), the cells appear as a homogeneous population with cell diameter of about 12 microns and a high nuclear/cytoplasm ratio, with 3–4 nucleoli/nucleolus. The cells stained intensely bright with rhodamine 123 (FIG. 1B) characteristic of fast growing cells. The cells also stained positively for N-myc and c-myc (FIG. 1E; red and 1F; green), respectively.

Figure 2A:
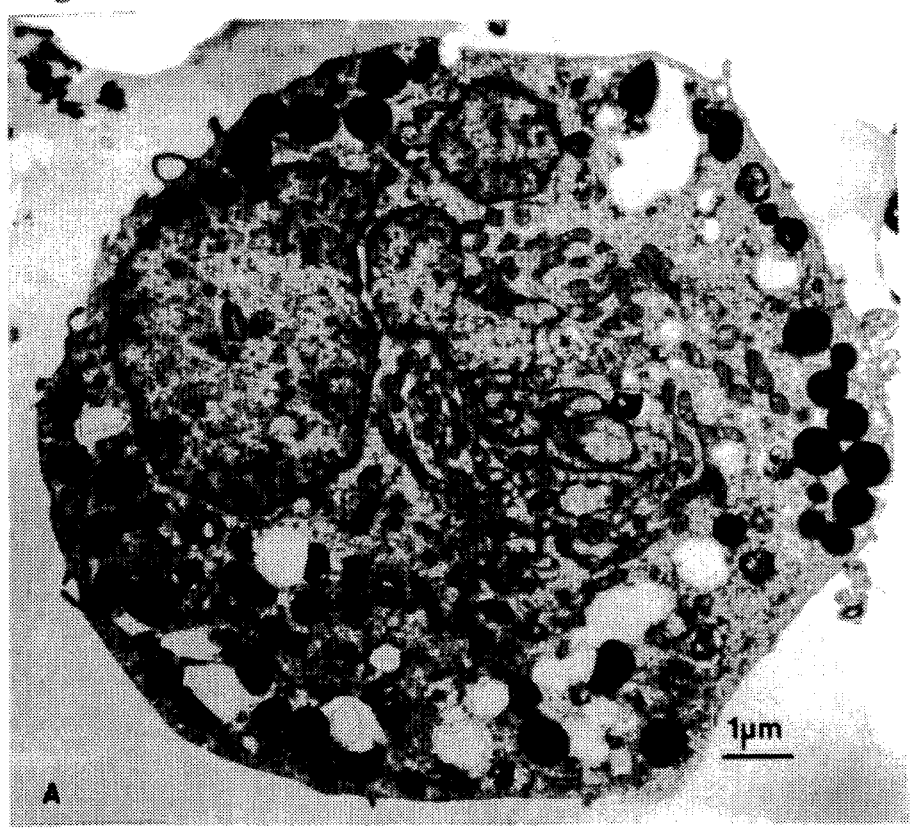
FIG. 2A is a transmission electron micrograph of the cells of the present invention.
Figure 2B:
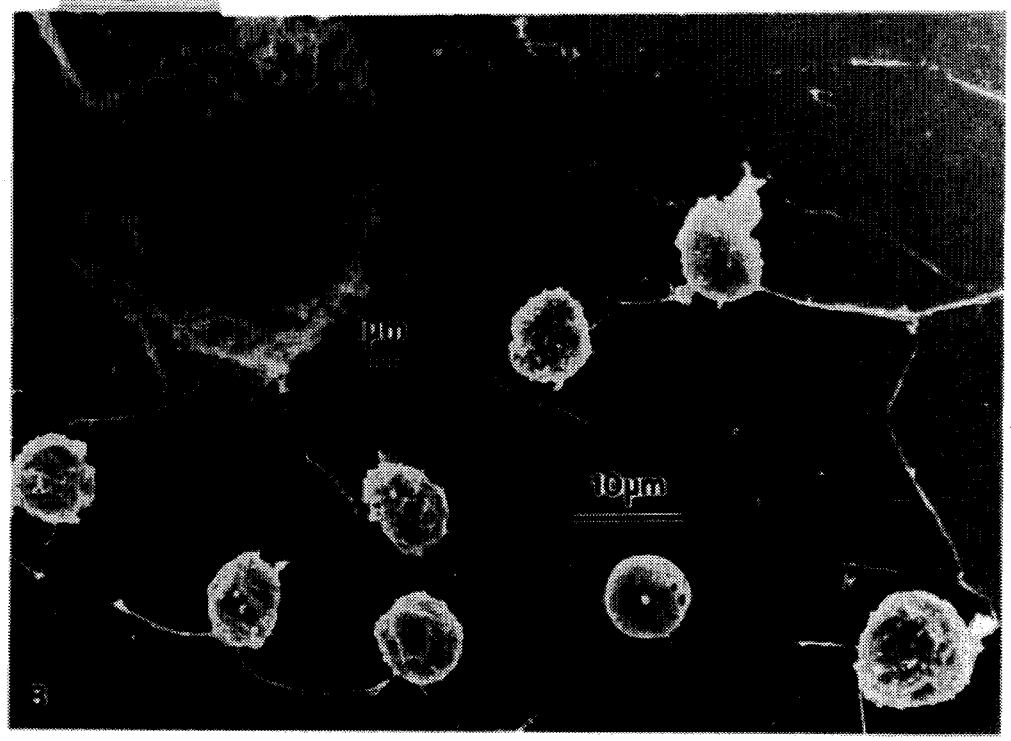
FIG. 2B is a scanning electron micrograph of the cells of the present invention.

Analysis of the distribution of the cells within the cell cycle revealed a high proportion of S-phase cells (44%) and $G_2/M$ (12%), in agreement with the short doubling time observed (9 h). Transmission electron microscopy (TEM) and scanning electron microscopy (SEM) revealed the ultrastructure typical of lymphoid blast cells, with numerous small mitochondria, many vacuoles and a large number of electron-dense secretory granules (FIG. 2A). Similarly, SEM studies disclosed the typical villous surface of a spherical lymphoid cell surface. Occasionally tiny filamentous processes could be seen (FIG. 2B).

Cytogenetic and molecular genetic characterization

Figure 3:
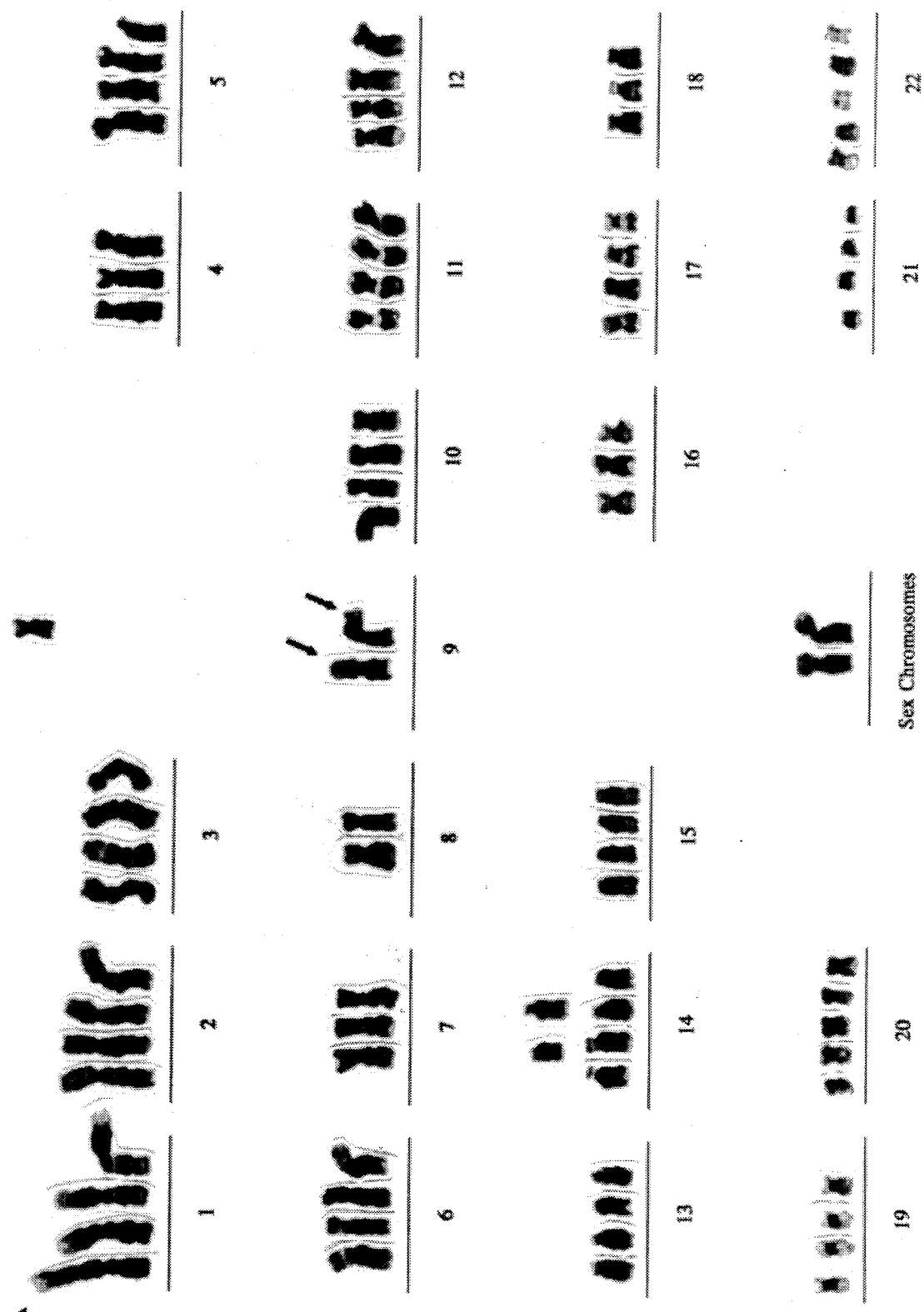
FIG. 3 depicts a representative karyotype of the cells of the present invention.

Analysis of DNA content by flow cytometry revealed a DNA index of 1.9 indicating a close to tetraploid DNA content. Similarly, karyotype analysis disclosed the presence of 85–87 chromosomes with an abnormality in one of the four chromosomes of chromosome 1 (homogeneous stained region: hsr); a deletion in the short arm of one of the four chromosomes of chromosome 5, an addition to the short arm of the two chromosomes of chromosome 9 and a marker chromosome. These abnormalities were seen in all karyotypes examined (20/20 for chromosome 1 and nearly all karyotypes (18/20) for chromosome 5 and 9 and the marker chromosome. A representative karyotype is shown in FIG. 3 (86; xx; hsr(1)(p32); del(5p); 9+,9+; marker).

Figure 4:
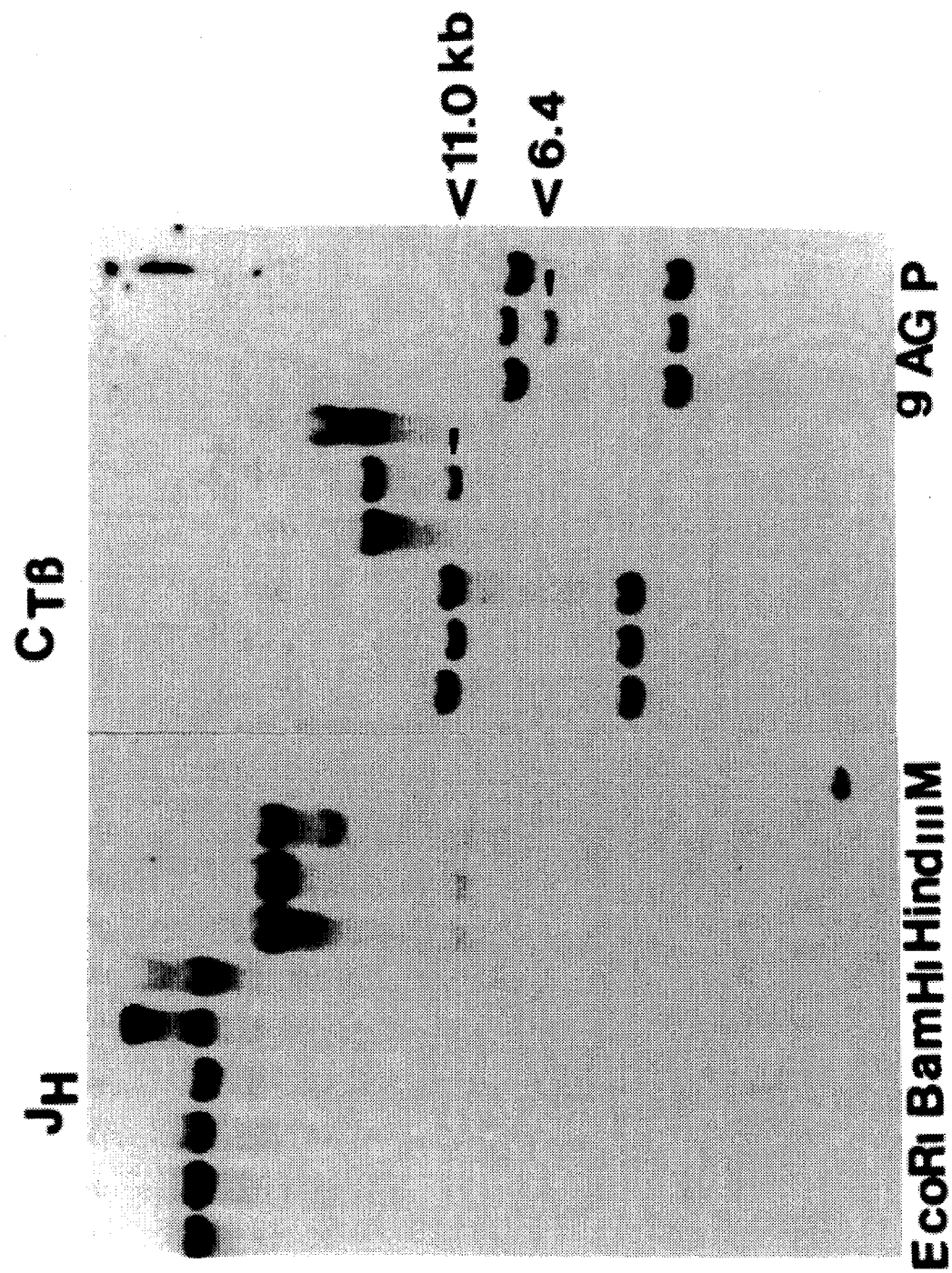
FIG. 4 depicts the results of probing for gene rearrangement showing second DNA bands, indicating that the cells of the present invention represent a monoclonal cell population with a T cell lineage gene rearrangement.
Figure 5A:
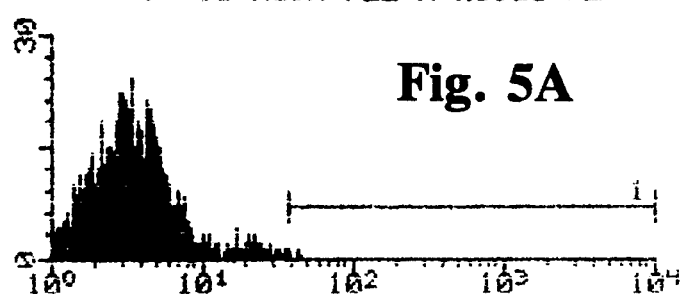
FIGS. 5(A–E) depict phenotyping of the cells of the present invention.
Figure 5B:
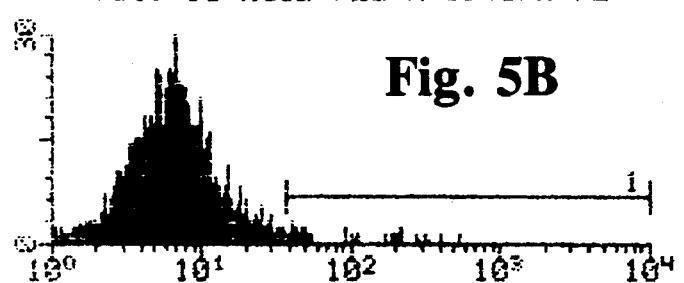
Figure 5C:
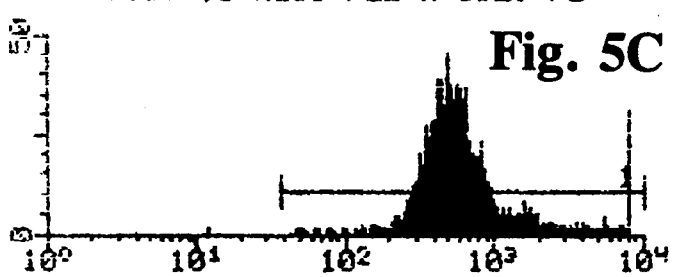
Figure 5D:
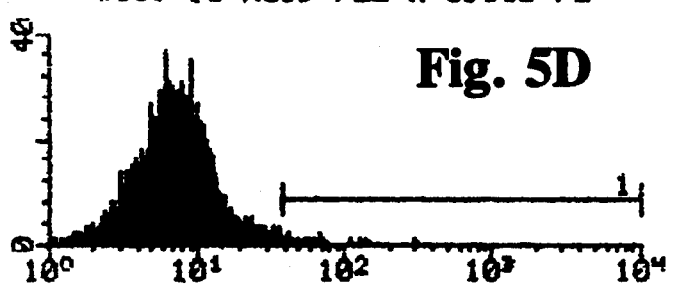
Figure 5E:
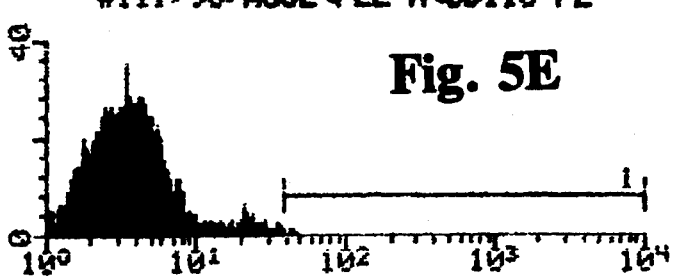
Figure 6B:
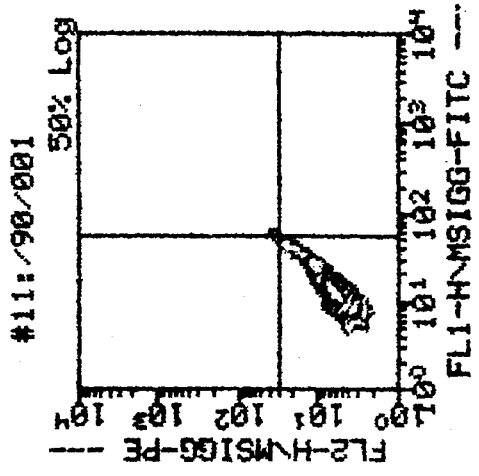
FIGS. 6(A–H) depict various dual staining of the cells of the present invention.
Figure 6D:
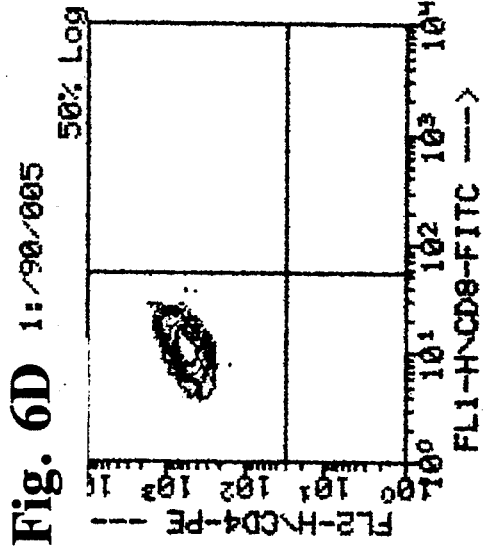
Figure 6A:
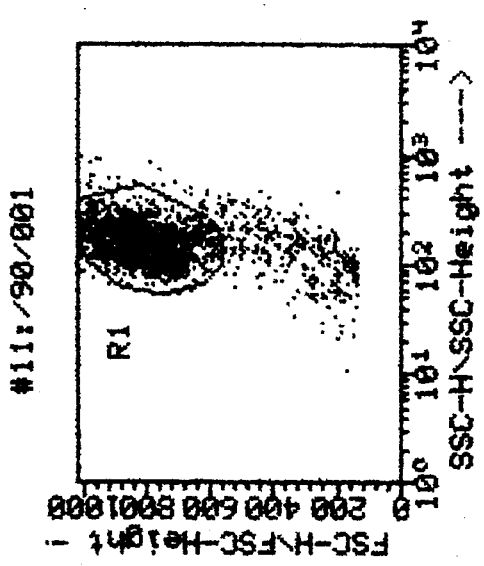
Figure 6C:
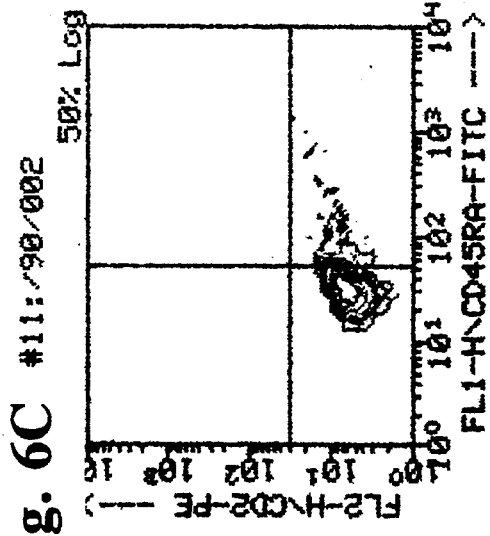
Figure 6E:
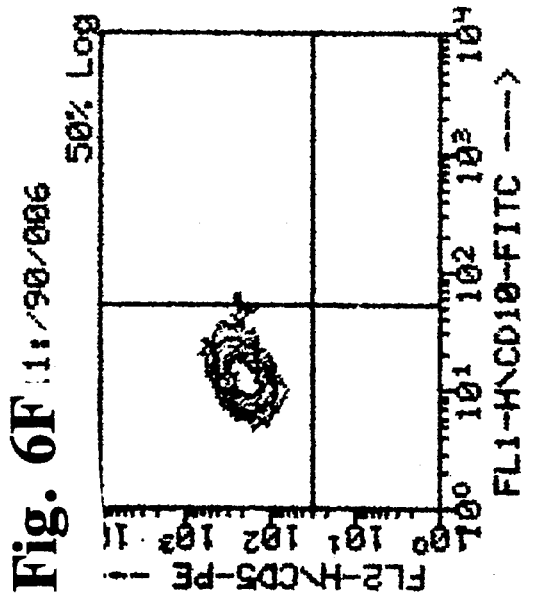
Figure 6F:
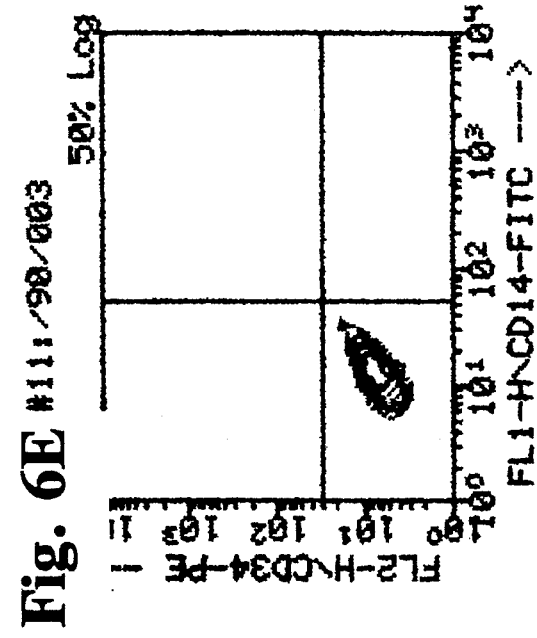
Figure 6G:
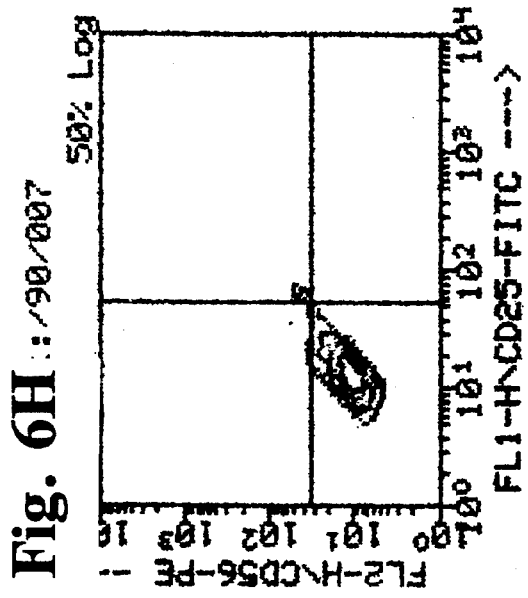
Figure 6H:
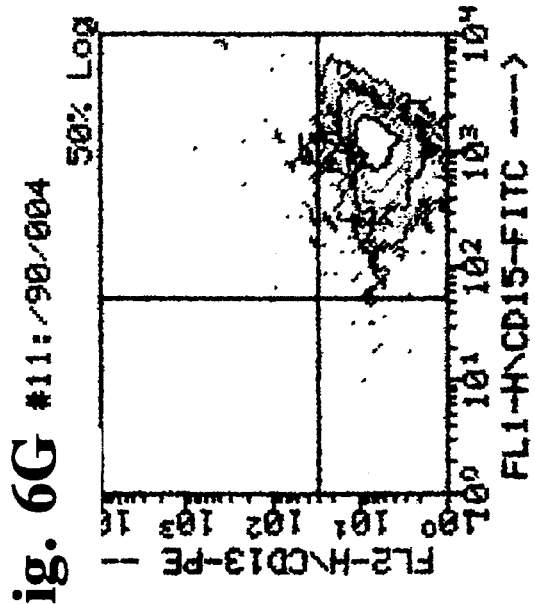
Figure 7A:
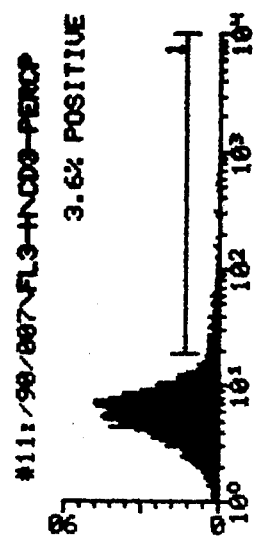
FIGS. 7(A–F) depict phenotyping of the cells of the present invention compared to controls.
Figure 7B:
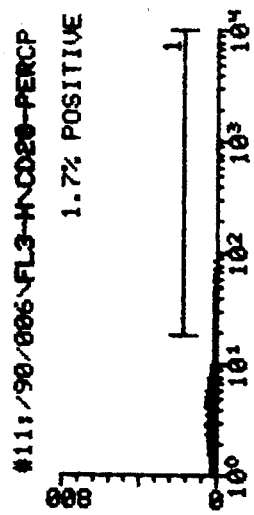
Figure 7C:
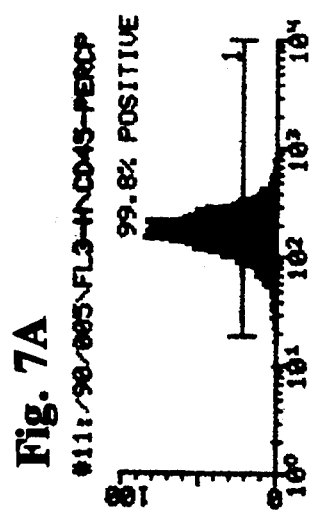
Figure 7D:
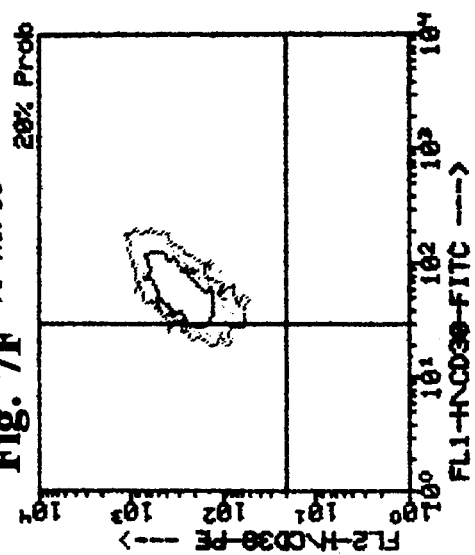
Figure 7E:
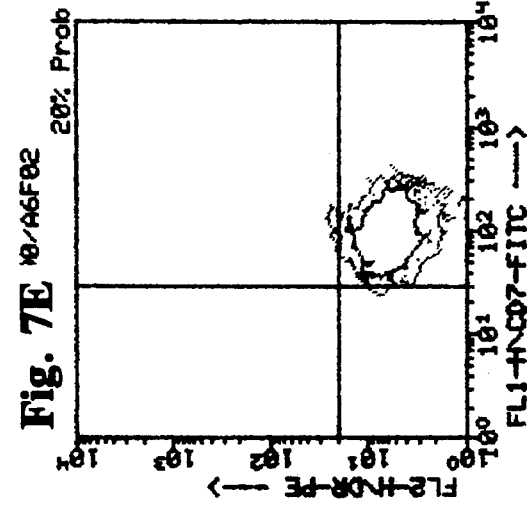
Figure 7F:
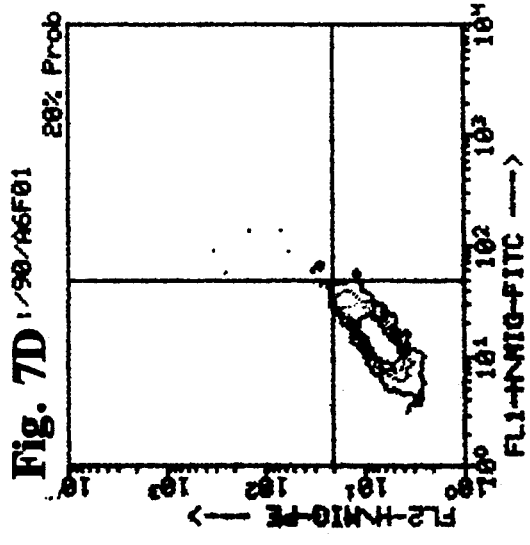

Gene rearrangement studies for the immunoglobulin gene, using the JH Probe, and T cell receptor gene, using the CT beta probe revealed T cell rearrangement in the beta gene, indicated by the appearance of a second DNA band of 11.0 kb (arrow) when the DNA was digested with the BamH1 restriction enzyme, and the appearance of a new band of 6.4 kb (arrow) following digestion with the Hind III restriction enzyme, FIG. 4(left panel, AG). At the same time, a germ line placental DNA (g) and DNA from a patient with unrearranged T cell receptor did not show any non-germline DNA bands. These results indicate that AG-F cells represent a monoclonal cell population with a T cell lineage gene rearrangement. No rearrangement was observed for the immunoglobulin gene (JH; left panel).

Immunophenotyping

Immunophenotyping of AG-F cells with antibodies to typical lymphoid markers revealed the expression of markers characteristic of an early T cell with T-helper/inducer phenotype, positive for CD4; CD5; CD7; CD29; CD71; CD38; CD45 and CD45RO (FIGS. 5–7). Interestingly, typical pan T-markers, such as CD2, CD3, and HLA-DR. as well as the receptor for IL-2 (CD25) were negative. Markers for myeloid and B cell lineage (except for early myeloid, CD33) were negative (FIGS. 5–7). On the other hand, markers typical of Hodgkin's lymphoma and large anaplastic cell lymphoma were positive (CD15 and CD30). The results are summarized in Table I.

TABLE I

| Immunophenotyping of AG-F cell line. | | | |
|---|---|---|---|
| Cluster Designation | Antigen Specificity | Positive Cells (%) | Source |
| 1a | thymocytes | <1.0 | Coulter ($T_6$) |
| 2 | pan-T-cells | <1.0 | Gentrak |
| 3 | pan-T-cells | 3.6 | B.D. |
| 4 | T-helper/inducer | 99.9 | B.D. |
| 5 | pan-T-cells | 99.2 | Gentrak |
| 7 | early T-cells | 95.2 | Gentrak |
| 8 | T-cytotoxic/suppressor | <1.0 | B.D. |
| 10 | CALLA | <1.0 | Dako |
| 11a | LFA-1 | <1.0 | Dako |
| 11b | granulocytes/monocytes | <1.0 | B.D. |
| 11c | granulocytes/NK-cells | <1.0 | B.D. |
| 13 | myeloid cells | <1.0 | Coulter (My7) |
| 14 | myeloid/monocytes | <1.0 | Gentrak |
| 15 | HL/granulocytes - | 99.3 | Gentrak (pm-81) |
| 18 | subunit of CD11 | <1.0 | Dako |
| 19 | pan B-cells | <1.0 | Dako |
| 20 | pan B-cells | 1.7 | B.D. |
| 25 | IL-2 receptor | <1.0 | Gentrak |
| 29 | β-1 integrin receptor/ | 99.9 | Coulter (4B4) |

TABLE I-continued

Immunophenotyping of AG-F cell line.

| Cluster Designation | Antigen Specificity | Positive Cells (%) | Source |
|---|---|---|---|
| | activated T-cells | | |
| 30 | Ki-1 antigen/HL | 93.6 | Dako |
| 33 | myeloid cells | 99.9 | Coulter (My9) |
| 34 | stem cells | <1.0 | B.D. |
| 38 | activated T-cells, thymocytes | 96.2 | B.D. |
| 45 | leukocytes | 99.9 | B.D. |
| 45RA | non-activated T-cells | 1.1–10.7 | Gentrak |
| 45RO | activated T-helper | 99.0 | Dako (UCHL-1) |
| 56 | NK-cells | 2.0 | B.D. |
| 71 | transferrin receptor | 99.8 | Gentrak |
| TdT | terminal deoxy thymidine transferase | <1.0 | Gentrak |
| HLA-ABC | histocompatibility-antigen (class I) | 99.2 | Gentrak |
| HLA-DR | histocompatibility antigen (class II) | 3.4 | Gentrak |

Staining and analysis of AG-F cells was done as described in the Materials and Method section. CALLA—common type ALL antigen; NK—natural killer cells; B.D.—Becton Dickinson; HL—Hodgkin's lymphoma.

Secretion of lymphokines

Table I summarizes the results obtained from analyses of culture medium for secreted lymphokines. Among the lymphokines secreted were IL-6 (0.6 ng/ml), IL-10 (1.6 ng/ml); IL-8 (1.6 ng/ml) and GM-CSF (0.3 ng/ml). IL-5 and IL-4 were secreted at lower levels (0.08 ng/ml). On the other hand, IL-1α and IL-1β, IL-2, gamma interferon, and PNS [alpha] were not secreted by AG-F cells (Table II). Analysis of AG-F cells for mRNA transcripts for various lymphokines reveals the presence of transcripts for IL-6, GM-CSF and IL-4. MRNA transcripts for IL-1α, IL-1β, IL-2, IL-3 and G-CSF were not detected (Table II).

TABLE II

Secretion of lymphokines by AG-F cells.

| Lymphokine | mRNA* | Expression protein (ng/ml)** |
|---|---|---|
| IL-1α | – | >0.03-$^R$ |
| IL-1β | – | >0.03-$^E$ |
| IL-2 | – | >0.03-$^E$ |
| IL-3 | – | >0.03-$^E$ |
| IL-4 | + | 0.08-$^E$ |
| IL-5 | N.D. | 0.08-$^E$ |
| IL-6 | + | 0.6-$^E$ |
| IL-8 | N.D. | 1.6-$^R$ |
| IL-10 | N.D. | 1.6-$^E$ |
| G-CSF | – | N.D. |
| GM-CSF | + | 0.3-$^R$ |
| INF-gamma | N.D. | >0.03-$^E$ |
| TNF-α | N.D. | >0.03-$^E$ |

*mRNA transcripts were determined on total RNA extracts by Northern blots analyses, as described in the Materials and Methods Section.
**Secretion of lymphokines was determined in spent medium by ELISA (E) or RIA (R) as described in the Materials and Methods Section.
N.D.—not done.

EXAMPLE 2

Induction of cell adherence and process formation in AG-F cells

Figure 8A:
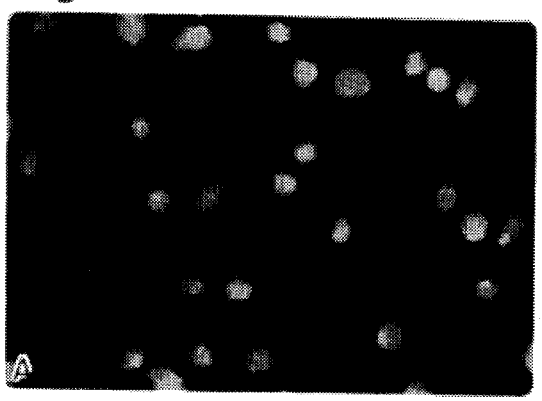
FIGS. 8(A–H) depict the induction of cell adherence and process formation in the cells of the present invention.
Figure 8B:
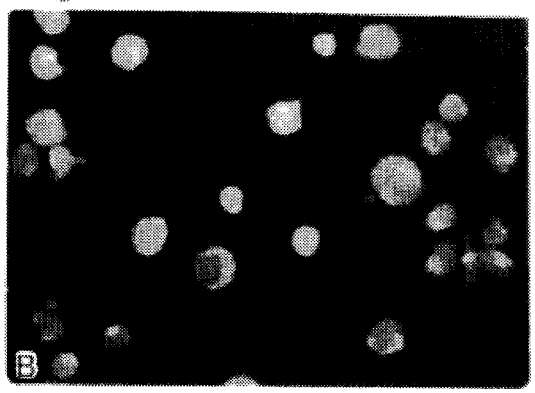
Figure 8C:
Figure 8D:
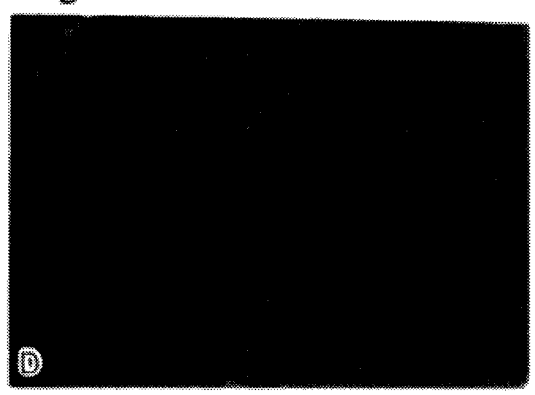
Figure 8E:
Figure 8F:
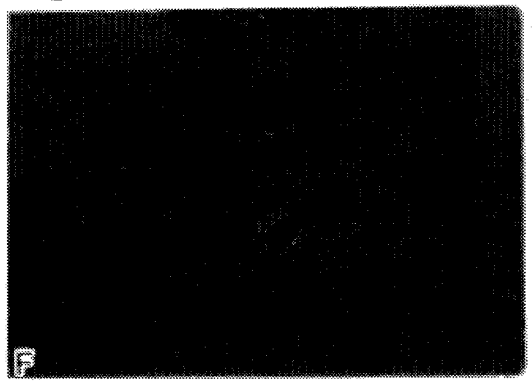
Figure 8G:
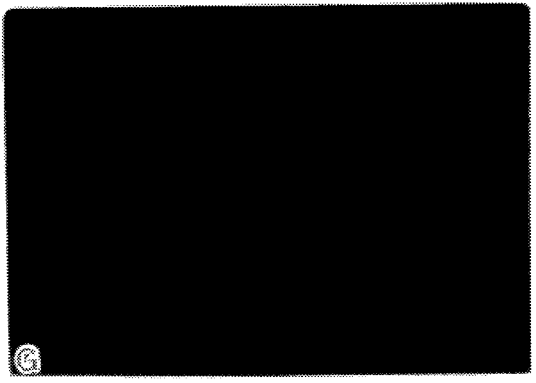
Figure 8H:
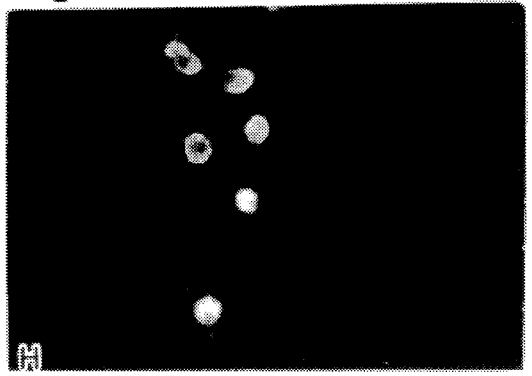

FIG. 8A and FIG. 8B depict AG-F cells following brief exposure (24 h) to fibronectin (8A) or collagen (8B). Cells were stained with FDA (vital stain, for cell cytoplasm). FIGS. 8C and 8D depict cells treated for three days as in 8A and 8B, but stained with the Giemsa stain. Processes were seen in fibronectin treated cells in about 20% of cells. With collagen, cells were adherent (>50%) but remained round even after addition of phorbol myristate acetate (PMA). FIGS. 8E and 8F depict cells treated with both fibronectin and PMA for three days. Many more cells were adherent and with larger processes (>80%), as seen in FDA (vital stain, 8E) and in fixed, Giemsa stained cells (8F). Addition of PMA alone did not cause significant cell adherence or process formation. The combined treatment with PMA and fibronectin resulted in a great reduction in staining for c-myc (8H), but not of N-myc (8G), (compare to FIG. 1E, 1F).

AG-F cells treated for 72 h with PMA and fibronectin exhibited marked increase in the expression of surface adhesion molecules (CD11a, CD11b, CD18) and the cell surface markers— CD45-RO, whereas, CD15 and CD30 antigens expression decreased markedly (Table III).

TABLE III

Immunophenotyping of adherent AG-F cells.

| Cluster Designation | Antigen Specificity | Positive cells (%) |
|---|---|---|
| 2 | pan-T | <1 |
| 3 | pan-t | <1 |
| 4 | T-helper/inducer | 99 |
| 5 | pan-T cell | 98 |
| 7 | early T-cell | 60** |
| 8 | cytotoxic/suppressor T-cell | <1 |
| 10 | CALLA | <1 |
| 11a | LFA-1 | 70* |
| 11b | granulocyte/monocyte | 86* |
| 11c | granulocyte/monocyte/NK cell | <1 |
| 13 | myeloid cell | 8* |
| 14 | myeloid/monocyte | <1 |
| 15 | HL/granulocyte - | 29** |
| 18 | subunit of CD11 | 96* |
| 19 | pan-B | <1 |
| 20 | pan-B | <1 |
| 25 | IL-2 receptor - | <1 |
| 29 | integrin receptor/activated T-cell | 92 |
| 30 | HL/ki1 antigen | <1** |
| 33 | myeloid cell | 84 |
| 34 | stem cell | 2 |
| 38 | activated T-cell/thymocyte | 72 |
| 45RA | non-activated T-cell | <1 |
| 45RO | activated T-cell | 96* |
| 56 | NK cell | 3 |
| HLA-DR | histocompatibility antigen | 13* |

Cell adherence was obtained by 4-day incubation with PMA and fibronectin.
Other legends are as in table 1.
*increased expression in adherent cells.
**decreased expression in adherent cells.

AG-F cells treated for three days with PMA and fibronectin exhibited distinct ultrastructural changes, such as decreased number of vacuoles, mitochondria and secretory granules (FIG. 9A), with obvious long process formation. Formation of processes was much more evident when viewed in the SEM micrographs (9B, 9C and 9D) where clear migration of the cell was observed (FIG. 9B, left to right; 9D, right to left).

EXAMPLE 3

Expression of mRNA transcripts to oncogenes

Large amounts of mRNA transcripts for N-RAS, P53, c-myc, and less for N-myc, were observed in a Northern Blot analysis of total RNA extracted from AG-F cells (FIG. 10, lane 1, right panel).

For comparison, RNA extracted from the neuroblastoma cell line SK-N-SH is shown in lane 2, right panel. The left panel represents the ethidium bromide staining of total RNA and used as a loading control.

EXAMPLE 4

Augmentation of antibody secretions

Hybridomas for anti-c-myc, anti-N-myc and anti-P53 were cultured in either regular medium or in a medium containing 50% v/v AG-F Conditioned medium. The supernatant was then assayed for antibody production three days later. Antibody production was determined by ELISA and the specificity was determined by using AG-F cells as target cells in an immunofluorescence staining and flow cytometry as described above [Gazitt, et al. *J Immunol Methods* 1992; 148:171–178.] (Table IV).

TABLE IV

Augmentation of antibody secretion in various hybridomas by AG-F cells conditioned medium (50% v/v).

| HYBRIDOMA | SECRETION µg/ml | TITER OF SPECIFIC AG BINDING |
|---|---|---|
| Anti c-myc | 2.4 µg/ml | 1:2 |
| (+AG-F Sup.) | 6.5 µg/ml | 1:8 |
| Anti N-myc | 1.1 µg/ml | 1:1 |
| (+AG-F Sup.) | 2.4 µg/ml | 1:3 |
| Anti P53 | 0.3 µg/ml | 3:1 |
| (+AG-F Sup.) | 0.9 µg/ml | 1:1 |

EXAMPLE 5

Augmentation of Cell growth and mitotic index by AG-F conditioned medium

Tissue samples from thirty patients diagnosed with either chronic lymphocytic leukemia (CML), myelodisplastic syndrome (MDS), non-Hodgkin's lymphoma (NHL), lymphoma (Lym.), acute lymphoblastic leukemia (ALL), or chronic lymphocytic leukemia (CLL) were cultured in AG-F conditioned medium and compared with cultures grown in a commercially available Giant Cell Tumor (GCT)-conditioned medium. The GCT-conditioned medium is of considerable assistance in the study of, for instance, bone marrow cytogenetics. In eighty percent of the cases, AG-F conditioned medium was equal to or better than the commercially available medium (Table V.). With the apparent unavailability of the GCT-conditioned medium through the commercial source, AG-F conditioned medium may provide an economically viable alternative.

TABLE V

Augmentation of cell growth and mitotic index by AGF conditioned medium. Comparison with commercially available medium.

| Patient name | Diagnosis/ Karyotype | Mitotic Index* | Total cells analyzed |
|---|---|---|---|
| W. L. | CML/+8 | +/− | 20 |
| C. E. | Lym./N | + | 20 |
| S. X. | MPD/N | + | 20 |
| D. D. | CML/N | + | 10 |
| B. E. | MDS/N | − | 20 |
| A. S. | CML/(t9;22) | +/− | 5 |
| H. R. | CML/N | + | 20 |
| S. A. | Anemia/N | +/− | 20 |
| J. R. | Lym./N | + | 20 |
| P. E. | NHL/N | − | 20 |
| D. J. | Thrombocytosis/N | +/− | 20 |
| W. M. | Not defined/N | +/− | 20 |
| D. D. | ALL(t9;22) | + | 20 |
| H. C. | ALL/N | +/− | 20 |
| M. H. | MPD/N | +/− | 20 |
| M. L. | MDS/N | +/− | 20 |
| B. J. | MDS(t9;22) | +/− | 20 |
| P. K. | MDS/N | +/− | 20 |
| G. S. | Lym./+y | +/− | 20 |
| T. L. | Pancytopenia/N | +/− | 20 |
| S. B. | Lung Ca./N | +/− | 20 |
| C. P. | Thrombocytopenia/N | +/− | 20 |
| L. M. | MPD/N | +/− | 20 |
| L. L. | CML/(t9;22) | +/− | 15 |
| R. R. | NHL/N | +/− | 20 |
| S. D. | MDS/very abnormal | +/− | 20 |
| T. A. | Waldenstrom/N | − | 20 |
| N. C. | Thrombocytopenia/N | − | 20 |
| C. M. | CLL/N | + | 10 |
| M. F. | Leukocytosis/N | +/− | 20 |

*GCT = AGF (+/−); GCT superior than AGF (−); AGF superior than GCT (+). CML = chronic lymphocytic leukemia; MDS = myelodisplastic syndrome; NHL = non-Hodgkin's lymphoma; Lym. = lymphoma; ALL = acute lymphoblastic leukemia; CLL = chronic lymphocytic leukemia. Cell culture conditions, chromosome analysis and staining was done as described by Morgan et al. (Karyogram 14: 7–9, 1988). AGF conditioned medium (CM) was equal or better than GCT CM in 80% of cases.

EXAMPLE 6

Utilization of AG-F cells in the study of Human Herpesvirus-6

In a reported study of human B-lymphotropic virus (HBLV), also known as human herpesvirus-6 (HHV-6), the rate of infectivity in fresh normal mononuclear cells in vitro is quite low, less than 1% [Lusso P, et al. In vitro cellular tropism of human B-lymphotropic virus (human herpesvirus-6). Exp. Med. 1988; 167:1659–1670.]. The majority of the small uninfected cells die within the first week in, culture and must be removed at day six to eight by gradient centrifugation so that the cell viability is restored to >90%. The infected cells display phenotypic characteristics of immature T lymphocytes. Virtually all infected cell express the CD7 antigen, the earliest known T-lymphocytic marker along the intrathymic T cell differentiation pathway, as well as the CD5 antigen, a pan-T marker, and the CD2 antigen.

AG-F cell line has all the positive/negative markers except for CD2 which is negative in AG-F cells and positive in those cells of the study. Using AG-F cells would be an advantage because the AG-F cell is an earlier cell in development than the cells used in the reported study.

EXAMPLE 7

Utilization of AG-F cells in the study of retroviruses

At least one cell system has been developed for the reproducible detection of human T-lymphotropic retroviruses [Popovic M, Sarngadharan M, Read E, Gallo R. Detection, isolation, and continuous production of cytopathic retroviruses (HTLV-III) from patients with AIDS and Pre-AIDS. *Science* 1984;224:497–500.]. The establishment of T-cell populations that continuously grow and produce virus after infection opens the way to the routine detection of cytopathic variants of HTLV in AIDS patients and provides an opportunity for detailed immunological and molecular analyses of these viruses. The use of AG-F cell line should increase substantially the rate of infectivity because of the high CD4 and cell adherence properites of AG-F cell line.

What is claimed is:

1. The substantially pure human T cell line designated AGF, deposited with ATCC accession number CRL 11391.

* * * * *